United States Patent [19]

Schmieding

[11] Patent Number: 5,320,626
[45] Date of Patent: Jun. 14, 1994

[54] ENDOSCOPIC DRILL GUIDE

[75] Inventor: Reinhold Schmieding, Naples, Fla.

[73] Assignee: Arthrex Inc., Naples, Fla.

[21] Appl. No.: 836,720

[22] Filed: Feb. 19, 1992

[51] Int. Cl.$^5$ .............................................. A61F 5/04
[52] U.S. Cl. ...................................................... 606/96
[58] Field of Search ................. 606/96, 97, 98, 86–90

[56] References Cited

U.S. PATENT DOCUMENTS

| | | | |
|---|---|---|---|
| 4,273,117 | 6/1981 | Neuhauser | 606/80 |
| 4,686,972 | 8/1987 | Kurland | 604/96 |
| 5,112,337 | 5/1992 | Paulos et al. | 604/98 |
| 5,147,367 | 9/1992 | Ellis | 606/96 |
| 5,154,720 | 10/1992 | Trott et al. | 606/96 |

FOREIGN PATENT DOCUMENTS

| | | | |
|---|---|---|---|
| 240457 | 7/1987 | European Pat. Off. | |
| 281763 | 2/1988 | European Pat. Off. | 606/97 |
| 495487 | 7/1992 | European Pat. Off. | |

OTHER PUBLICATIONS

Howard Marans, MD, et al., *A New Femoral Drill Guide for Arthroscopically Assisted Anterior Cruciate Ligament Replacement*, 1992.

Darrel A. Penner, MD, et al., *An In Vito Study of Anterior Cruciate Ligament Graft Placement and Isometry*, 1988.

J. Mark Melhorn, MD, et al., "*The Relationship of the Femoral Attachment Site to the Isometric Tracking of the Anterior Cruciate Ligament Graft*," 1987.

D. I. Bylski-Austrow; et al., *Anterior Cruciate Ligament Replacements: A Mechanical Study of Femoral Attachment Location, Flexion Angle at Tensioning, and Initial Tension*, 1990.

Mohamed S. Hefzy, PhD., et al., *Factors Affecting the Region of Most Isometric Femoral Attachments*, 1989.

Magnus Odensten, MD, PhD., et al., *Functional Anatomy of the Anterior Cruciate Ligament and a Rationale for Reconstruction*, 1985.

Primary Examiner—Jerome L. Kruter
Attorney, Agent, or Firm—Ostrolenk, Faber, Gerb & Soffen

[57] ABSTRACT

An endoscopic drill guide for locating the proper position of a graft tunnel for endosteal fixation of a substitute ligament or graft between two bones, such as a tibia and a femur. The drill guide includes a shaft with an offset hook. The drill guide is inserted through a graft tunnel drilled in the tibia, and the offset hook is positioned so that it engages the posterior aspect of the femoral notch. A guide pin is inserted through the drill guide and driven into the femur to properly position drilling of a graft tunnel in the femur.

16 Claims, 2 Drawing Sheets

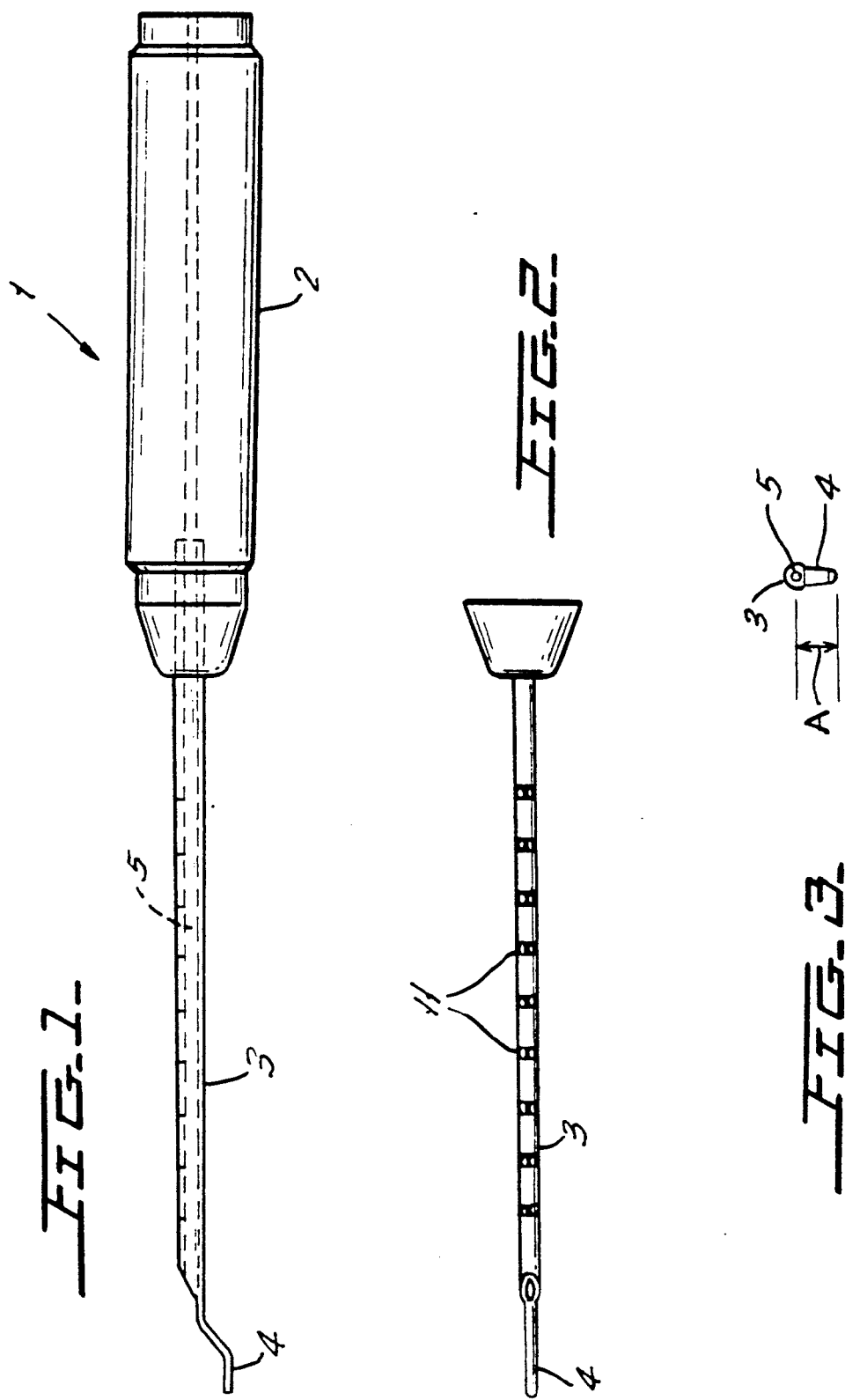

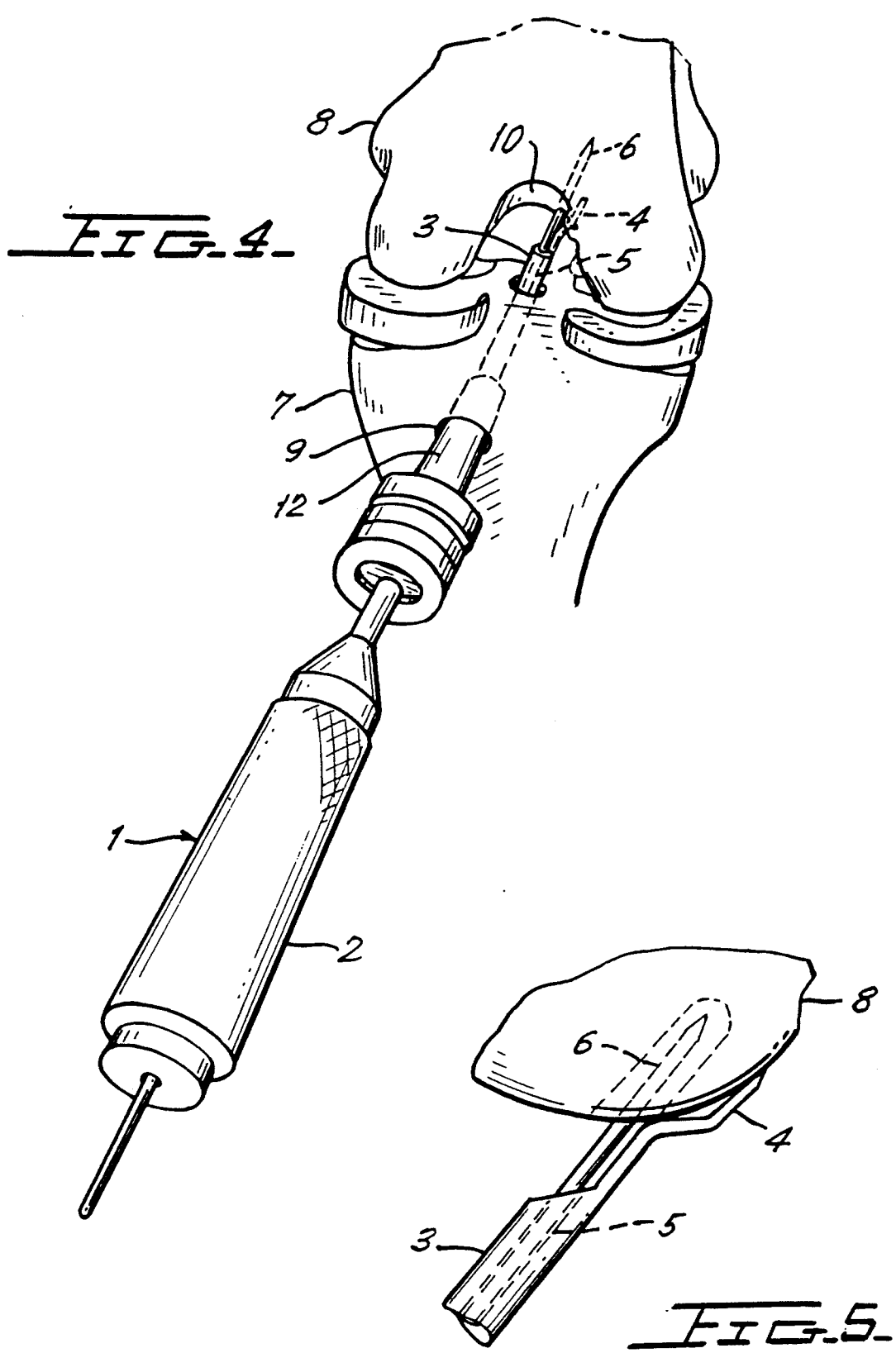

ENDOSCOPIC DRILL GUIDE

BACKGROUND OF THE INVENTION

1. Field of the Invention

The present invention relates to an endoscopic drill guide and, more specifically, to an endoscopic drill guide having an offset hook for properly locating the position to drill a tunnel for endosteal fixation of a substitute ligament or graft.

2. Description of the Related Art

When a ligament or tendon becomes detached from the bone, surgery is usually required to re-secure the ligament or tendon. Often, a substitute ligament or graft is attached to the bone to facilitate regrowth and permanent attachment. The reattachment procedure involves drilling of a graft tunnel between two bones, for example, the tibia and the femur.

To achieve optimal results, it is important that the graft tunnel be drilled at a particular angle and location through the tibia and femur. Ordinarily, an incision is made to access the proper area for drilling a tunnel through the tibia. A guide pin is placed through the incision and driven into the tibia. A drill is then placed over and guided by the guide pin during the drilling of the graft tunnel through the tibia.

A problem arises in locating the proper position for drilling the graft tunnel in the femur. The ideal location for the graft tunnel is 7 mm in front of the posterior aspect of the femoral notch. Ordinarily, the location for drilling the graft tunnel in the femur is determined in one of two ways.

The first method is to insert the guide pin through the incision and the graft tunnel in the tibia and into the femur. The drill is then placed over and guided by the guide pin during drilling of the graft tunnel in the femur. The problem with this method is that the femur is difficult to see through the graft tunnel in the tibia. Thus, determining the proper location for the graft tunnel in the femur must often be accomplished by guesswork.

The second method is to drill the graft tunnel in the femur in the opposite direction from the outside. Although this method is more accurate, it involves making a second incision which results in unnecessary fluid loss and an additional scar.

A further disadvantage of the above two methods is that neither permits testing of graft isometry or notch impingement prior to attachment of the graft. Such testing enables a more secure graft attachment, resulting in rapid healing and stronger regrowth.

SUMMARY OF THE INVENTION

The present invention overcomes the above-mentioned problems in the prior art by providing an endoscopic drill guide consisting of a shaft with an offset hook. The offset hook engages a notch in the femur and automatically aligns the shaft on the femur at a predetermined distance from the notch. For proper alignment of a drill guide for drilling a graft tunnel in a femur, the offset hook is laterally displaced from the center of the shaft by a distance of 7 mm, or alternatively by a distance of 6 mm, 5 mm, or anywhere in between depending on the application.

The shaft is cannulated for receiving a guide pin, the guide pin being pushed through the shaft and driven into the femur at the predetermined location relative to the notch. The guide pin serves to guide a cannulated drill to that location for drilling the graft tunnel.

The shaft is preferably provided with longitudinally spaced markings for indicating the required length of a graft to be passed through the tunnel, the markings being spaced in predetermined longitudinal increments of about 10 mm.

The drill guide is provided with a cannulated handle, preferably made of aluminum. The shaft and offset hook are preferably formed of a high tensile strength steel, such as Carpenter 630.

The present invention also relates to a method of using the cannulated drill guide to locate the proper position for drilling a tunnel for endosteal fixation of a graft between a first bone (such as a tibia) and a second bone (such as a femur), the method including the steps of:

drilling a tunnel through the first bone;
inserting the cannulated drill guide through the tunnel and engaging a notch in the second bone with the offset hook of the drill guide, the offset hook aligning the drill guide at a predetermined location relative to the position of the notch;
pushing a guide pin through the drill guide and driving it into the second bone at the predetermined location; and
drilling a graft tunnel into the second bone at the location of the guide pin.

The method of the present invention includes the optional step of inserting a cannula with a silicon dam into the tunnel prior to the insertion of the drill guide to reduce fluid loss from said tunnel.

Advantageously, the present invention permits testing of graft isometry and notch impingement with the offset hook in place. If too much movement is observed during graft isometry testing, the position of the offset hook in the notch can be adjusted. Potential notch impingement can also be evaluated by extending the joint into 5° of hyperflexion. If the shaft of the drill guide restricts hyperextension, a notchplasty can be performed and impingement checked again.

Other features and advantages of the present invention will become apparent from the following description of the invention which refers to the accompanying drawings.

BRIEF DESCRIPTION OF THE DRAWINGS

FIG. 1 shows the drill guide of the present invention.
FIG. 2 is a top view of the shaft of the drill guide.
FIG. 3 is a front view of the offset hook of the present invention.
FIG. 4 shows the drill guide in use.
FIG. 5 is an expanded view of the offset hook in use with the guide pin inserted.

DETAILED DESCRIPTION OF THE PREFERRED EMBODIMENT

Referring first to FIG. 1, the drill guide of the present invention, indicated generally by reference numeral 1, consists of a tubular shaft 3 with an offset hook 4 at one end. A handle 2 is preferably press fit onto the opposite end of shaft 3. Handle 2, preferably formed with aluminum, and shaft 3 are both cannulated for receiving a guide pin 6, as discussed in further detail below.

The offset hook 4 is a substantially flat extension of one end of the tubular shaft 3. The hook 4 is S-shaped such that it initially extends in a direction parallel to the longitudinal axis of the shaft 3, then curves away from the longitudinal axis, then curves back to extend in a direction parallel to the longitudinal axis of the shaft, thus defining the S-shape.

The hook 4 is preferably about 2.4 mm wide and about 1.14 mm thick. The length of the hook 4, from the end of the tubular shaft, is about 19 mm. The offset portion, which is offset from the longitudinal axis of the shaft 3 and extends parallel to the shaft 3, is preferably about 6.6 mm in length.

Offset hook 4 is laterally displaced from the center of shaft 3, due to the S-shaped structure described above, preferably by a distance A of 7 mm (as shown in the front view of FIG. 3), so as to provide proper positioning of guide pin 6 when offset hook 4 is engaged against the femoral notch. In alternative embodiments, offset hook 4 is displaced at a lateral distance A of 5 mm, 6 mm, or any distance between 5 mm and 7 mm. The offset hook 4 and tubular shaft 3 are preferably formed of a chromium-nickel alloy.

Referring now to the top view of drill guide 1 in FIG. 2, shaft 3 is shown as including longitudinally spaced markings 11. Markings 11 are laser engraved in rings around shaft 3, preferably at 10 mm. increments. When shaft 3 is inserted into the graft tunnel of the tibia (as discussed below), the number of exposed markings 11 provides an indication of the length of the graft required.

Referring now to FIGS. 4 and 5, the method of using the drill guide of the present invention for preparing a tibia 7 and femur 8 for endosteal fixation of a ligament will now be described, it being understood that endosteal fixation of a substitute ligament or graft is well known in the art. See, e.g. Kurosaka et al., "*A Biochemical Comparison of Different Surgical Techniques of Graft Fixation in Anterior Cruciate Ligament Reconstruction,*" Am. Jour. Sports Med. Vol. 15, No. 3, pp. 225–229, herein incorporated by reference.

As is the usual practice in the art, a graft tunnel 9 is first drilled in the tibia 7 through a previously prepared incision. A cannula 12 with a silicon dam is preferably inserted in tunnel 9 to prevent excessive fluid loss. The drill guide 1 of the present invention is then inserted through cannula 12 and graft tunnel 9 until offset hook 4 engages the posterior aspect of the femoral notch 10.

Advantageously, notch impingement and graft isometry can be evaluated with the drill guide in place. If the shaft 3 restricts hyperextension, a notchplasty can be performed and impingement checked again. If too much movement is observed during graft isometry testing, the offset hook 4 can be adjusted farther superior or lateral in the notch 10 and isometry tested again.

After testing is completed and adequate results have been attained, guide pin 6 is inserted through the cannula 5 of drill guide 1 and driven into femur 8. As shown in FIG. 5, offset hook 4 automatically aligns the positioning of guide pin 6 in femur 8 at the proper distance (preferably 7 mm) from the rear aspect of femoral notch 10. Once guide pin 6 is in place, drill guide 1 is removed and a reamer with a cannulated head (not shown) is placed over the guide pin for drilling the graft tunnel in femur 8.

The previous example is for illustrative purposes only. Many other variations and modifications and other uses of the present invention will become apparent to those skilled in the art. It is preferred, therefore, that the present invention be limited not by the specific disclosure herein, but only by the appended claims.

What is claimed is:

1. An endoscopic drill guide for locating a tunnel to be drilled through a femur for endosteal fixation of a ligament graft between the femur and a tibia, said drill guide comprising:
   (a) a cannulated shaft, said cannulated shaft being cannulated along its entire length and having a centrally located longitudinal axis; and
   (b) an offset hook located on a distal end of said cannulated shaft and offset from said longitudinal axis of said cannulated shaft for engaging a notch in a femur and for aligning said cannulated shaft at a predetermined offset location in said notch.

2. An endoscopic drill guide according to claim 1, wherein said shaft is cannulated for receiving a guide pin, said guide pin being inserted through said shaft and driven into said femur at said predetermined location in to said notch.

3. An endoscopic drill guide according to claim 1, wherein said offset hook is laterally offset from said longitudinal axis of said cannulated shaft by a distance of about 7 mm.

4. An endoscopic drill guide according to claim 1, wherein said offset hook is laterally offset from said longitudinal axis of said cannulated shaft by a distance of about 6 mm.

5. An endoscopic drill guide according to claim 1, wherein said offset hook is laterally offset from said longitudinal axis of said cannulated shaft by a distance of about 5 mm.

6. An endoscopic drill guide according to claim 1, wherein said cannulated shaft is provided with longitudinally spaced markings for indicating the required length of said graft.

7. An endoscopic drill guide according to claim 6, wherein said markings are spaced in predetermined longitudinal increments of about 10 mm.

8. An endoscopic drill guide according to claim 1, further comprising a handle attached to said annulated shaft.

9. An endoscopic drill guide according to claim 8, wherein said handle is aluminum.

10. An endoscopic drill guide according to claim 1, wherein said cannulated shaft and said offset hook are formed of a high tensile strength steel.

11. A method of locating the proper position for drilling a tunnel for endosteal fixation of a graft between a first bone and a second bone, said method comprising the steps of:
   drilling a tunnel through said first bone;
   inserting a cannulated drill guide comprising a cannulated shaft having an offset hook located on a distal end thereof through said tunnel and engaging a notch in said second bone with said offset hook, said shaft being cannulated along its entire length and having a centrally located longitudinal axis, said offset hook being offset from said. longitudinal axis of said cannulated shaft for aligning the drill guide at a predetermined offset location in the notch; and
   drilling a tunnel into said second bone at the predetermined offset location.

12. A method according to claim 11, further comprising the step of inserting a cannula with a silicon dam into said tunnel prior to the insertion of said drill guide to reduce fluid loss from said tunnel.

13. A method according to claim 11, wherein said first bone comprises a tibia and said second bone comprises a femur.

14. A method according to claim 11, wherein said predetermined location comprises a lateral offset of approximately 7 mm.

15. A method according to claim 11, wherein said predetermined location comprises a lateral offset of approximately 6 mm.

16. A method according to claim 11, wherein said predetermined location comprises a lateral offset of approximately 5 mm.

* * * * *